United States Patent [19]
Bhattacharyya

[11] Patent Number: 4,806,345
[45] Date of Patent: Feb. 21, 1989

[54] CROSS-LINKED CATIONIC POLYMERS FOR USE IN PERSONAL CARE PRODUCTS

[75] Inventor: Bhupati R. Bhattacharyya, Downers Grove, Ill.

[73] Assignee: Nalco Chemical Company, Naperville, Ill.

[21] Appl. No.: 800,471

[22] Filed: Nov. 21, 1985

[51] Int. Cl.⁴ .................. A61K 7/06; A61K 7/08; A61K 7/48
[52] U.S. Cl. .................................. 424/70; 424/61; 424/78; 424/81; 514/844; 514/873; 514/880
[58] Field of Search ............. 424/70, 59, 60, 81, 424/78, DIG. 1; 521/312

[56] References Cited

U.S. PATENT DOCUMENTS

| | | | |
|---|---|---|---|
| 3,917,817 | 11/1975 | Vanlerberghe et al. | 424/81 |
| 3,934,595 | 1/1976 | Madrange et al. | 132/7 |
| 3,946,749 | 3/1976 | Papantoniou | 132/7 |
| 3,959,237 | 5/1976 | Blank | 424/81 |
| 4,012,501 | 3/1977 | Farber | 424/47 |
| 4,048,301 | 9/1977 | Papantoniou et al. | 424/70 |
| 4,272,511 | 6/1981 | Papantoniou | 424/47 |
| 4,282,203 | 8/1981 | Jacquet et al. | 424/47 |
| 4,348,380 | 9/1982 | Jacquet et al. | 424/47 |
| 4,362,715 | 12/1982 | Strianse et al. | 424/78 |
| 4,401,650 | 8/1983 | Salamone | 424/78 |
| 4,478,853 | 10/1984 | Chaussee | 424/78 |
| 4,500,337 | 2/1985 | Young et al. | 424/78 |
| 4,508,705 | 4/1985 | Chaudhuri et al. | 424/78 |
| 4,528,111 | 7/1985 | Su | 424/78 |

Primary Examiner—Dale R. Ore
Attorney, Agent, or Firm—Joan I. Norek; John G. Premo; Donald G. Epple

[57] ABSTRACT

Personal care compositions are provided which have as a thickening agent a lightly cross-linked cationic vinyl addition polymer. Such compositions include water, at least one cosmetically-active agent, and such thickening agent, preferably one derived from the polymerization of a cationic vinyl addition monomer, acrylamide, and a small amount of a difunctional vinyl addition monomer for cross-linking purposes. Alternatively, the cross-linking functionality can be provided by the incorporation of an anionic vinyl addition monomer into the polymer.

16 Claims, No Drawings

CROSS-LINKED CATIONIC POLYMERS FOR USE IN PERSONAL CARE PRODUCTS

TECHNICAL FIELD OF THE INVENTION

The present invention is in the technical field of thickening agents for water-based compositions, and more particularly in the field of thickening agents for water-based personal care products, such as shampoos, hair treatment compositions of both the rinse-off and leave-on type, hand lotions, and the like, compositions containing such agents, and thickening methods.

BACKGROUND OF THE INVENTION

Many industries have a need for materials that can increase the viscosity of aqueous-based compositions such as aqueous solutions or dispersions or emulsions having an aqueous continuous phase. In many instances, a particular viscosity is desired or necessary for ease in handling, dispensing, or otherwise using a product. Coating compositions, such as latex paints, must have sufficient viscosity to avoid excessive dripping from the applicator. Personal care products, which are often applied by hand, generally must have sufficient viscosity to cling to the hand of the user, and then to the hair, or skin, or other point of application. For instance, if a hand lotion had a fluidity approaching that of water, until completely dried a significant portion would be transferred to and deposited on anything the user may touch. A watery hair-set lotion would run through the user's fingers and off the hair during application. To such type of formulations a separate ingredient or ingredients are often added to increase viscosity to the desired level. Such materials are called thickeners or thickening agents.

It is desirable that such thickening agents provide the desired viscosity at a low add-on level to minimize cost. It is desirable that such agents be compatible with other ingredients in the formulation at use level. Thus the nature of a given thickener must be taken into consideration together with that of the other components of the composition. Moreover, desired activity of the thickener at low use levels may diminish potential incompatibilities. It is also desirable to have available a group of thickening agents from which to select one to provide a particular viscosity level at a particular add-on level.

In the personal care product industry thickening agents based on anionic polymers are widely known, such as carboxy vinyl polymers.

There are sufficient compatibility problems between such anionic polymers and other formulation components that effective alternatives are being sought.

DISCLOSURE OF THE INVENTION

The present invention provides personal care composition including, as a thickening agent, a lightly cross-linked cationic vinyl addition polymer. Such polymers may be homopolymers of certain quaternary ammonium salts of vinyl addition monomers, in particular the quaternary ammonium salt of dimethylaminoethylmethacrylate. Other suitable cationic vinyl addition monomers from which such polymer could be formed include the quaternary ammonium salts of dimethylaminoethylacrylate, diallyldimethyl ammonium chloride, and methylacrylamidopropyltrimethyl ammonium chloride. Such polymers also include the polymerization of one or more of such cationic vinyl additon monomers together with other vinyl addition monomers having suitable reactivity ratios for such polymerizations. These other vinyl addition monomers that may be incorporated into such polymers may be nonionic, cationic, or anionic, or combinations thereof. A particularly useful monomer for such polymerizations is acrylamide. As expalined below, a particularly useful combination of monomers for such polymerizations is a combination of acrylamide and acrylamidomethyl propane sulfonic acid.

Such polymers are lightly cross-linked with a suitable cross-linking agent, such as a difunctional vinyl addition monomer polymerized together with the polymeric formulation. Preferred cross-linking agents are certain polyethylene glycol diacrylic esters. The light cross-linking can also be provided by an ionic cross-linking mechanism, by the inclusion of a suitable anionic monomer together with the cationic monomer in the vinyl addition polymerization utilized for the preparation of the polymers used in the present invention. The cross-linking can also be provided by a combination of both such mechanisms.

The cationic thickeners utilized in the present invention have been found to have highly desirable viscosity development efficiency, and in preferred embodiment have been found superior to those of commercial carboxy vinyl polymer thickeners.

PREFERRED EMBODIMENTS OF THE INVENTION

The present invention, in one embodiment, is a personal care composition including at least one cosmetically-active agent in a water-base, together with a lightly cross-linked cationic vinyl addition polymer as a thickening agent. In another embodiment, the present invention is a method of thickening a water-based personal care composition including at least one cosmetically-active agent, by admixing therewith an effective amount of a lightly cross-linked cationic vinyl addition polymer to increase the viscosity of the composition.

By cosmetically-active agent is meant herein any material applied to the body, typically to the skin, hair, or nails, for the cosmetic treatment thereof. Such agents, include emollients and lubricants for softening or smoothing, surfactants for cleansing and other purposes, natural or synthetic polymers for various purposes including the topical coating of the hair to build body or to enhance setting characteristics, and the like. Such agents include, without limitation, mineral oils, glycerin, beeswax, lanolin, acetylated lanolin, stearic acid, palmitic acid, cetyl alcohol, sodium lauryl sulfate, sodium salts of olefin sulfonates, various proteins and polymeric sugars, and the like. This list is intended to exemplitive only and not limiting as to the materials that are encompassed by the term cosmetically-active agent. In water-based personal care compositions the water is a vehicle for application to some part of the body of some cosmetically-active agent that will have a cosmetic effect of some type, whether such effect is a softening or cleansing or strengthening or body enhancing effect. It is the intent here to include within the terms cosmetically-active agent any and all of such materials that are provided for a cosmetic effect.

The personal care compositions of the present invention can also include combinations of cosmetically-active agents of various types, coloring agents, fragrances, preservatives, and the like.

As mentioned above, the lightly cross-linked cationic vinyl addition polymers used in the present invention can be formed not only from wholly cationic vinyl addition monomers, but may also include nonionic monomers, particularly acrylamide, and certain anionic vinyl addition monomers, particularly an alkali metal salt of acrylamidomethyl propane sulfonic acid. When such an anionic vinyl addition monomer is incorporated into such polymer, it is incorporated at a mole percent that is less than the mole percent of the cationic vinyl addition monomer therein.

A preferred embodiment of the invention is a personal care composition having as a thickening agent a lightly cross-linked cationic vinyl addition polymer derived from the polymerization of 5 to 100 mole percent of a cationic vinyl addition monomer, 0 to 90 mole percent of acrylamide, and from 0.005 to 0.05 weight percent of a difunctional vinyl addition monomer. In more preferred embodiment, the difunctional vinyl addition monomer is a polyethylene glycol diacrylic ester having a molecular weight of from 300 to 3,000, and the cationic vinyl addition monomer is a quaternary ammonium salt of dimethylaminoethylmethacrylate. In highly preferred embodiment, the lightly cross-linked cationic vinyl addition polymer is derived from the polymerization of from 15 to 70 mole percent of a quaternary ammonium salt of dimethyl/aminothylmethacrylate and from 30 to 85 mole percent of acrylamide, and from 0.005 to 0.025 weight percent of the polyethylene glycol diacrylic ester, particularly where the polyethylene glycol diacrylic eester is polyethylene glycol dimethacrylate. It has been found that such a personal care composition wherein the thickener is even more particularly such a polymer derived from about 50 mole percent of dimethylaminoethylmethacrylate mmonium chloride and about 50 mole percent of acrylamide provides a highly desirable viscosity and rheological properties at a one weight percent addition level.

In other embodiment, the personal hair compositions of the present invention may contain, as the thickening agent, a lightly cross-linked vinyl addition polymer derived from the polymerization of from 15 to 60 mole percent of a cationic vinyl addition monomer, from 25 to 80 mole percent of acrylamide and from 2 to 30 mole percent of an anionic vinyl addition monomer. In preferred embodiment, the cationic vinyl addition monomer is a quaternary ammonium salt of dimethylaminoethylmethacrylate, and the anionic vinyl addition monomer isan alkali metal salt of acrylamidomethyl propane sulfonic acid. A more preferred embodiment, the thickening agent of the personal care composition is derived from the polymerization of from 20 to 50 mole percent of a quaternary ammonium salt of dimethylaminoethylmethacrylate, from 40 to 75 mole percent of acrylamide and from 5 to 10 mole percent of an alkalic metal salt of acrylamidomethyl propane sulfonic acid. Although cross-linking is provided therein by the inclusion of both cationic and anionic functionalities, such polymers may also further include from 0.005 to 0.05 weight percent of a difunctional vinyl addition monomer, particularly a polyethylene glycol diacrylic ester having a molecular weight of from 300 to 3,000.

The present invention also provides a method of thickening a personal care composition comprising admixing with a mixture of water and at least one cosmetically-active agent an effective amount of a lightly cross-linked cationic vinyl addition polymer to increase the viscosity thereof. In preferred embodiment, the lightly cross-linked cationic vinyl addition polymer is derived from the polymerization of from 5 to 100 mole percent of a cationic vinyl addition monomer, from 0 to 90 mole percent of acrylamide, and from about 0.005 to 0.05 weight percent of a difunctional vinyl addition monomer. In other preferred embodiment, the lightly cross-linked cationic vinyl addition polymer is derived from the polymerization of from 15 to 60 mole percent of a cationic vinyl addition monomer, from 25 to 80 mole percent of acrylamide and from 2 to 30 mole percent of an anionic vinyl addition monomer. Such anionic-containing vinyl addition monomer may further include from 0.005 to 0.05 weight percent of a difunctional vinyl addition monomer.

The present invention also includes a thickening agent for water-based compositions comprising a lightly cross-linked vinyl addition polymer containing from 15 to 60 mole precent of a cationic vinyl addition monomer, from 25 to 80 mole percent of acrylamide and from 2 to 30 mole percent of an anionic vinyl addition monomer. In preferred embodiments, the cationic vinyl addition monomer is a quaternary ammoinum salt of dimethylaminoethylmethacrylate, the anionic vinyl addition monomer is an alkali metal salt of acrylamidomethyl propane sulfonic acid, and the lightly cross-linked cationic vinyl addition polymer further contains from 0.005 to 0.01 weight percent of a polyethylene glycol diacrylic ester having a molecular weight of 300 to 3,000.

All of the above-delineated polymers may be prepared using conventional solution polymerization techniques or preferably methods in which water-soluble vinyl addition monomers are polymerized in the form of water-in-oil emulsions. In the latter instance, the water-in-oil latex polymerization product is typically inverted, utilizing conventional techniques, to release the polymer into some solution or composition having water as the continuous phase. In any application in which the oil of the continuous phase of the polymerization latex is to be separated from the polymer itself, the polymer may be isolated by precipitation from the emulsion latex, for instance with ethanol.

EXAMPLES 1 TO 27

In the following examples various cationic vinyl addition polymers useful in the present invention were prepared utilizing the water-i-oil emulsion technique described above. The relative mole percentages of the various monomers that were incorporated into the polymer are expressed in the table below without regard to the branching or cross-linking agent, although such agents were added to the monomer solutions before polymerization and thus incorporated into the polymer, because such agents are added at only a fraction of a mole percentage. Hence the amount of cross-linking agent is expressed in terms of weight percentage based on total polymer. In each of the examples, the viscosities of aqueous solutions of the polymer were measured at various polymer concentrations using a Brookfield viscometer LVT Model at 12 rpm at ambient room temperature. The viscosity development efficiencies shown by the viscosity measurements set forth below demonstrate the efficiencies of these polymers as thickeners, and particularly for personal care compositions the presence of a polyethylene glycol diacrylic ester has been shown to provide desired short rheological properties at low use levels without pititous characteristics.

In the following Tables I and II, the following abbreviations are utilized. "NaAMPS" for sodium salt of acrylamidomethyl propane sulfonic acid; "DMAEM-MCQ" for the methyl chloride quaternary ammonium salt of dimethylaminoethylmethacrylate; "AcAm" for acrylamide; "MBA" for methylene bis acrylamide; and "PEG 600 DMA" for polyethylene glycol dimethylate having an ethylene oxide content of about 12 units.

0.2 weight percent concentration, the viscosity was about 2,400 cps; at 0.4 weight percent concentration, the viscosity was about 17,000; and at 0.5 weight percent concentration the viscosity was about 33,000 cps; and at 1.0 weight percent concentration, the viscosity was about 50,000 cps.

The polymers used in the present invention may be used singly or in combination to provide the desired viscosity.

TABLE I

| Example No. | Mole % Monomer | | | Wt. % of Cross-Linking Monomer | | Polymer Solution Viscosity (cps) at Specified Polymer Concentration | | | |
|---|---|---|---|---|---|---|---|---|---|
| | Na AMPS | DMAEM—MCQ | AcAm | MBA | PEG 600 DMA | 0.18% | 0.35% | 0.7% | 1.05% |
| 1 | 10 | 50 | 40 | 0.000 | 0.010 | 100.00 | 1187.50 | 18000.00 | 3000.0 |
| 2 | 10 | 50 | 40 | 0.000 | 0.010 | 17.50 | 137.50 | 6150.00 | 28500.0 |
| 3 | 5 | 20 | 75 | 0.000 | 0.000 | 675.00 | 2275.00 | 4300.00 | 7500.0 |
| 4 | 10 | 30 | 60 | 0.000 | 0.000 | 350.00 | 1700.00 | 4000.00 | 5000.0 |
| 5 | 5 | 30 | 65 | 0.000 | 0.000 | 1375.00 | 1800.00 | 3800.00 | 3600.0 |
| 6 | 10 | 50 | 40 | 0.000 | 0.000 | 800.00 | 1775.00 | 2700.00 | 4800.0 |
| 7 | 20 | 50 | 30 | 0.000 | 0.000 | 12.50 | 187.50 | 1412.50 | 3200.0 |
| 8 | 20 | 50 | 30 | 0.005 | 0.000 | 12.50 | 75.00 | 700.00 | 2475.0 |
| 9 | 5 | 20 | 75 | 0.000 | 0.010 | 5.00 | 50.00 | 600.00 | 19250.0 |
| 10 | 10 | 50 | 40 | 0.005 | 0.000 | 2.50 | 12.50 | 237.50 | 5500.0 |
| 11 | 5 | 15 | 80 | 0.000 | 0.010 | 5.00 | 15.00 | 82.50 | 357.5 |
| 12 | 10 | 50 | 40 | 0.000 | 0.050 | 12.50 | 17.50 | 37.50 | 1025.0 |
| 13 | 5 | 20 | 75 | 0.000 | 0.050 | 6.25 | 18.75 | 25.00 | 37.5 |
| 14 | 30 | 40 | 30 | 0.000 | 0.000 | 6.25 | 12.50 | 18.75 | 25.0 |
| 15 | 10 | 30 | 60 | 0.000 | 0.050 | 3.75 | 5.00 | 7.50 | 15.0 |

TABLE II

| Example No. | Mole % Monomer | | | Wt. % of Cross-Linking Monomer | | Polymer Solution Viscosity (cps) at Specified Polymer Concentration | | | |
|---|---|---|---|---|---|---|---|---|---|
| | Na AMPS | DMAEM—MCQ | AcAm | MBA | PEG 600 DMA | 0.18% | 0.35% | 0.7% | 1.05% |
| 16 | 0 | 15 | 85 | 0.0 | 0.001 | 202.50 | 6650.00 | >100000.00 | >100000.00 |
| 17 | 0 | 15 | 85 | 0.0 | 0.010 | 125.00 | 5250.00 | >100000.00 | >100000.00 |
| 18 | 0 | 15 | 85 | 0.0 | 0.005 | 35.00 | 1075.00 | >100000.00 | >100000.00 |
| 19 | 0 | 50 | 50 | 0.0 | 0.015 | 250.00 | 21500.00 | 92500.00 | >100000.00 |
| 20 | 0 | 50 | 50 | 0.0 | 0.010 | 2375.00 | 33000.00 | 89000.00 | >100000.00 |
| 21 | 0 | 50 | 50 | 0.0 | 0.025 | 50.00 | 11200.00 | 88000.00 | >100000.00 |
| 22 | 0 | 25 | 75 | 0.0 | 0.010 | 275.00 | 26750.00 | >50000.00 | >50000.00 |
| 23 | 0 | 15 | 85 | 0.0 | 0.015 | 262.50 | 20750.00 | 47500.00 | 100000.00 |
| 24 | 0 | 70 | 30 | 0.0 | 0.010 | 1737.50 | 15500.00 | 40000.00 | 87000.0 |
| 25 | 0 | 50 | 50 | 0.0 | 0.005 | 2400.00 | 26000.00 | 38000.00 | 49500.0 |
| 26 | 0 | 25 | 75 | 0.0 | 0.005 | 2100.00 | 17000.00 | 36250.00 | 46000.0 |
| 27 | 0 | 100 | 0 | 0.0 | 0.010 | 1775.00 | 7750.00 | 11250.00 | 18000.0 |

EXAMPLE 28

The polymer of Example 20 above was incorporated as a thickener in both a leave-on hair treatment and in a rinse-off hair treatment at a level of 1 weight percent based on tota weight of the personal care product. Upon test use of both compositions separately, good setting was obtained for both. The lightly cross-linked cationic polymer was deemed an acceptable alternative to the typical carboxy vinyl polymers typically used as thickening agents in such compositions in their commercial form. The same polymer was also tested for use in a hand lotin, as a diluent for one-half (½) of the actives. A very creamy viscous lotion with good skin feel was obtained.

To give a reference frame to the various viscosity development sufficiencies set forth above in Tables I and II above, two commercial thickeners were tested of the carboxy vinyl polymer types for viscosity development efficiency, utilizing the same model Brookfield Viscometer at 12 rpm. For such thickener sold under the tradename of CARBOPOL 941 by B. F. Goodrich, viscosity was only slightly more than 1000 cps at 0.1 weight percent concentration, rising to somewhat less than 10,000 cps at a 1.0 weight percent concentration. For CARBOPOL 934, also sold by B. F. Goodrich, at

INDUSTRIAL APPLICABILITY OF THE INVENTION

The present invention is applicable to those industries, particularly the personal care industry, in which a thickening agent for water-based solutions, dispersions, or emulsions is desired.

I claim:

1. A personal care composition including:
   a water base;
   at least one cosmetically-active agent; and
   up to about 1.0 weight percent of a thickening agent consisting esentially of a lightly cross-linked cationic vinyl polymer derived from the polymerization of from 5 to 100 mole percent of a cationic vinyl addition monomer, from 0 to 90 mole percent of acyrlamide, and from 0.005 to 0.05 weight percent of a difuncitional vinyl addition monomer, wherein said cationic vinyl addition monomer is a quaternary ammonium salt of dimethylaminoethylmethacrylate.

2. The personal care composition of claim 1 wherein said difunctional vinyl additional monomer is a polyethylene glycol diacrylic ester having a molecular weight of from 300 to 3,000.

3. The personal care composition of claim 2, wherein said lightly cross-linked cationic vinyl addition polymer is derived from the polymerization from 15 to 70 mole percent of a quaternary ammonium salt of dimethylaminoethylmethacrylate and from 30 to 85 mole percent of acrylamide, and from 0.005 to 0.025 weight percent of said polyethylene glycol diacrylic ester.

4. The personal care composition of claim 3 wherein said polyethylene glycol diacrylic ester is a polyethylene glycol dimethacrylate.

5. The personal care composition of claim 4 wherein said lightly cross-linked cationic vinyl addition polymer includes about 50 mole percent of dimethylaminoethylmethacrylate ammonium chloride and about 50 mole percent of acrylamide.

6. A method of thickening a personal care composition comprising:
admixing with water and at least one cosmetically-active agent up to about 1.0 weight percent of a lightly cross-linked cationic vinyl addition polymer consisting essentially of a polymer derived from the polymerization of from 5 to 100 mole percent of a cationic vinyl additional monomer, from 0 to 90 mole percent of acrylamide, and from 0.005 to 0.05 weight percent of a difunctional vinyl addition monomer,
wherein said cationic vinyl addition polymer is a quaternary ammonium salt of dimethylaminoethylmethacrylate.

7. A personal care composition including: a water base;
at least one cosmetically-active agent; and
up to about 1.0 weight percent of a thickening agent comprising a lightly cross-linked cationic vinyl addition polymer consistng essentially of a polymer derived from the polymerization of from 15 to 60 mole percent of a quaternary ammonium salt of dimethylaminoethylmethacrlate, from 25 to 80 mole percent of acrylamide, and form 2 to 30 mole percent of an anionic vinyl addition monomer,
wherein the mole percent of said anionic vinyl addition monomer is less than the mole percent of said quaternary ammonium salt of dimethylaminoethylmethacrylate.

8. The personal care composition of claim 7 wherein said anionic vinyl addition monomer is an alkali metal salt of acrylamidomethyl propane sulfonic acid.

9. The personal care composition of claim 8 wherein said lightly cross-linked cationic vinyl addition polymer includes from 20 to 50 mole percent of a quaternary ammonium salt of dimethylaminoethylmethacrylate, from 40 to 75 mole percent of acrylamide and from 5 to 10 mole percent of an alkali metal salt of acrylamidomethyl propane sulfonic acid.

10. The personal care composition of claim 9 wherein said lightly cross-linked cationic vinyl addition polymer further includes from 0.005 to 0.05 weight percent of a difunctional vinyl addition monomer.

11. The personal care composition of claim 10 wherein said difunctional vinyl addition monomer is a polyethylene glycol diacrylic ester having a mclecular weight of from 300 to 3,000.

12. A method of thickening a personal care composition comprising:
admixing with water and at least one cosmetrically-active agent up to about 1.0 weight percent of a lightly cross-linked cationic vinyl addition polymer to increase the viscosity thereof wherein said lightly cross-linked cationic vinyl addition polymer consists essentially of a polymer derived from the polymerization of from 15 to 60 mole percent of a quaternary amonium salt of dimethylaminoethylmethacrylate, from 25 to 80 mole percent of acrylamide and from 2 to 30 mole percent of an anionic vinyl addition monomer,
wherein teh mole percent of said anionic vinyl addition monomer is less tahn the mole percent of said quaternary ammonium salt of dimethylaminoethylmethacrylate.

13. The method of claim 12 wherein said lightly cross-linked cationic vinyl addition polymer further includes from 0.005 weight percent of a difunctional vinyl addition monomer.

14. A thickening agent for water-based compositions comprising:
a lightly cross-linked vinyl addition polymer consisting essentially of a polymer derived from polymerization of from 15 to 60 mole percent of a cationic vinyl addition monomer, from 25 to 80 mole percent of acrylamide and form 2 to 30 mole percent of an anionic vinyl addition monomer,
wherein said cationic vinyl addition monomer is a quaternary ammonium salt of dimethylaminoethylmethacrylate,
and wherein the mole percent of said anionic vinyl addition monomer is less tahn the mole percent of said quaternayr ammonium salt of dimethylaminoethylmethacrylate.

15. The thickening agent of claim 14 wherein said anionic vinyl addition monomer is an alkali metal salt of acrylamidomethyl propane sulfonic acid.

16. The thickening agent of claim 14 wherein said lightly cross-linked cationic vinyl addition polymer further contains from 0.005 to 0.01 weight percent of a polyethylene glycol diacrylic ester having a molecular weight of 300 to 3,000.

* * * * *

UNITED STATES PATENT AND TRADEMARK OFFICE
CERTIFICATE OF CORRECTION

PATENT NO. : 4,806,345

DATED : Feb. 21, 1989

INVENTOR(S) : Bhupati R. Bhattacharyya

It is certified that error appears in the above-identified patent and that said Letters Patent is hereby corrected as shown below:

In Col. 6, in Claim 1, at line 60, cancel "acyrlamide" and substitute therefor -- acrylamide --. In Col. 7, in Claim 7, at line 40, cancel "dimethylaminoethylmethacrlate" and substitute therefor -- dimethylaminoethylmethacrylate --, and at line 41, cancel "form" and substitute therefor -- from --. In Col. 8, in Claim 12, at line 24, cancel "teh" and substitute therefor -- the --, and at line 25, cancel "tahn" and substitute therefor -- than --. In Col. 8, in Claim 14, at line 38, cancel "form" and substitute therefor -- from --, and at line 44, cancel "tahn" and substitute therefor -- than --,

UNITED STATES PATENT AND TRADEMARK OFFICE
CERTIFICATE OF CORRECTION

PATENT NO. : 4,806,345

DATED : Feb. 21, 1989

INVENTOR(S) : Bhupati R. Bhattacharyya

Page 2 of 2

It is certified that error appears in the above-identified patent and that said Letters Patent is hereby corrected as shown below:

and at line 45, cancel "quaternayr" and substitute therefor -- quaternary --.

Signed and Sealed this

Fifth Day of June, 1990

Attest:

HARRY F. MANBECK, JR.

*Attesting Officer*

*Commissioner of Patents and Trademarks*

(12) REEXAMINATION CERTIFICATE (4265th)
United States Patent
Bhattacharyya

(10) Number: US 4,806,345 C1
(45) Certificate Issued: Feb. 6, 2001

(54) CROSS-LINKED CATIONIC POLYMERS FOR USE IN PERSONAL CARE PRODUCTS

(75) Inventor: Bhupati R. Bhattacharyya, Downers Grove, IL (US)

(73) Assignee: S. C. Johnson & Son, Inc., Racine, WI (US)

Reexamination Request:
No. 90/005,415, Jul. 6, 1999

Reexamination Certificate for:
Patent No.: 4,806,345
Issued: Feb. 21, 1989
Appl. No.: 06/800,471
Filed: Nov. 21, 1985

Certificate of Correction issued Jun. 5, 1990.

(51) Int. Cl.[7] .............................. A61K 47/32; A61K 7/04; C08F 30/04; C08F 12/30
(52) U.S. Cl. .................... 514/772.4; 514/844; 514/873; 514/880; 424/61; 424/70.28; 526/240; 526/287
(58) Field of Search .................. 424/70.1, 70.11, 424/70.28, 78.02; 514/844, 880, 881

(56) References Cited

U.S. PATENT DOCUMENTS

| | | | |
|---|---|---|---|
| 3,917,817 | * 11/1975 | Vanlerberghe et al. . | |
| 3,934,595 | * 1/1976 | Madrange et al. . | |
| 3,946,749 | * 3/1976 | Papantoniou . | |
| 3,959,237 | * 5/1976 | Blank . | |
| 3,990,459 | 11/1976 | Papantoniou | 132/7 |
| 4,012,501 | * 3/1977 | Farber . | |
| 4,048,301 | * 9/1977 | Papantoniou et al. . | |
| 4,111,922 | 9/1978 | Beede et al. | 526/292 |
| 4,163,092 | 7/1979 | Steckler | 526/292 |
| 4,272,511 | * 6/1981 | Papantoniou et al. . | |
| 4,282,203 | * 8/1981 | Jacquet et al. . | |
| 4,348,380 | * 9/1982 | Jacquet et al. . | |
| 4,362,715 | * 12/1982 | Strianse et al. . | |
| 4,401,650 | * 8/1983 | Salamone . | |
| 4,478,853 | * 10/1984 | Chaussee . | |
| 4,500,337 | * 2/1985 | Young et al. . | |
| 4,508,705 | * 4/1985 | Chaudhuri et al. . | |
| 4,528,111 | * 7/1985 | Su . | |
| 4,542,175 | 9/1985 | Fink et al. | 524/516 |
| 4,737,541 | 4/1988 | Stavenger et al. | 524/547 |

FOREIGN PATENT DOCUMENTS

| | | |
|---|---|---|
| 1037407 | 8/1958 | (DE) . |
| 2077750 | 12/1981 | (GB) . |

OTHER PUBLICATIONS

Chemical Abstracts (vol. 54, 17959–17690 of DE 1,037,407.

* cited by examiner

*Primary Examiner*—Thurman K. Page

(57) ABSTRACT

Personal care compositions are provided which have as a thickening agent a lightly cross-linked cationic vinyl addition polymer. Such compositions include water, at least one cosmetically-active agent, and such thickening agent, preferably one derived from the polymerization of a cationic vinyl addition monomer, acrylamide, and a small amount of a difunctional vinyl addition monomer for cross-linking purposes. Alternatively, the cross-linking functionality can be provided by the incorporation of an anionic vinyl addition monomer into the polymer.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *